United States Patent [19]

Oman

[11] Patent Number: 4,926,865

[45] Date of Patent: May 22, 1990

[54] MICROCOMPUTER-BASED NERVE AND MUSCLE STIMULATOR

[76] Inventor: Paul S. Oman, 4701 Island View Dr., Mound, Minn. 55364

[21] Appl. No.: 298,782

[22] Filed: Jan. 17, 1989

Related U.S. Application Data

[63] Continuation of Ser. No. 103,589, Oct. 1, 1987, abandoned.

[51] Int. Cl.⁵ ............................................. A61N 1/00
[52] U.S. Cl. .................................... 128/421; 128/783
[58] Field of Search ........................ 128/421, 422, 783

[56] References Cited

U.S. PATENT DOCUMENTS

| | | | |
|---|---|---|---|
| 4,210,151 | 7/1980 | Keller, Jr. | 128/421 |
| 4,338,945 | 7/1982 | Kosuqui et al. | 128/421 |
| 4,340,063 | 7/1982 | Maurer | 128/421 |
| 4,399,821 | 8/1983 | Bowers | 128/421 |
| 4,434,798 | 3/1984 | Tvnkoczy et al. | 128/421 |
| 4,598,713 | 7/1986 | Hansjürgens et al. | 128/421 |
| 4,612,934 | 9/1986 | Borkau | 128/421 |
| 4,688,575 | 8/1987 | Du Vall | 128/422 |
| 4,693,254 | 9/1987 | Mickiewicz et al. | 128/421 |

OTHER PUBLICATIONS

Melzack R. et al., "Pain Mechanisms: A New Theory," Science, vol. 150, pp. 971–979 (Nov. 19, 1965).
Schmidt, R. F., "Presynaptic Inhibition in the Vertebrate Central Nervous System," Ergebnisse der Physiologie, 63, pp. 20–86(1971).
Eriksson, M. et al., "Long Term Results of Peripheral Conditioning Stimulation as an Analygesic Measure in Chronic Pain," Pain, 6, pp. 335–347 (1979).
Sjolund, B. H. et al., "The Influence of Naloxone on Analgesia Produced by Peripheral Conditioning Stimulation," Brain Research, 173, pp. 295–301 (1979).
Mayer, D. J. et al., "Antagonism of Acupuncture Analgesia in Man by the Narcotic Antagonis Naloxone," Brain Research, 121, 368–372 (1977).
Hughes, J. et al., "Identification of Two Related Pentapeptides From the Brain with Potent Opiate agonist Activity," Nature, vol. 258, pp. 577–579 (Dec. 18, 1975).
Matsukura, S. et al., "The Regional Distribution of Immunoreactive Beta-Endorphin in the Monkey Brain," Brain Research, 159, pp. 228–233 (1978).
Mannheimer, J. S. et al., "Clinical Transcutaneous Electrical Nerve Stimulation," F. A. Davis Company, Philadelphia, PA, pp. 345–431 (1984).

Primary Examiner—Francis Jaworski
Assistant Examiner—George Manuel
Attorney, Agent, or Firm—Merchant, Gould, Smith, Edell, Welter & Schmidt

[57] ABSTRACT

A transcutaneous nerve stimulation device is provided with mircocomputer-based control of pulse duration, pulse repetition rate, stimulation duty cycle and modulation of pulse parameters. The microcomputer 2 monitors battery 15 voltage and patient manipulated controls 14 that select pulse current amplitude and also provides signals used for display on a liquid crystal display 10 of all relevant stimulation parameters and warning annuciators. The microcomputer 2 is sensitive to input controls for calculation of all stimulation parameters, other than current amplitude, only when a program control switch 18 is active. When the program control switch 18 becomes inactive, the selected control information is stored in non-volatile memory 4, thereby providing electronic isolation of programming controls. The preferred embodiment of the nerve stimulation device may be used either for pain relief or to facilitate muscle contractions, which has a variety of therapeutic applications.

12 Claims, 8 Drawing Sheets

MICROCOMPUTER-BASED NERVE AND MUSCLE STIMULATOR

This is a continuation of application Ser. No. 103,589, filed Oct. 1, 1987, and abandoned.

This invention relates generally to an apparatus and method for controlling pain and contracting muscle tissue through the use of transcutaneous electrical nerve stimulation. More particularly, the invention relates to a nerve stimulation apparatus and method wherein the characteristics of the stimulating signals are controlled by a microprocessor.

BACKGROUND OF THE INVENTION

The use of electrical energy for the control of pain is well known. Although the specific physiological explanations underlying electrically derived pain control are not fully understood, the effect is nonetheless real and provides a non-drug, non-surgical and non-psychiatric method of pain control which can be applied to a wide variety of painful conditions.

Transcutaneous electric nerve stimulation (TENS) is a proven and accepted means of providing relief from many kinds of acute and chronic pain symptoms. It is an attractive alternative to pharmaceuticals since it has no addictive properties and there are no known side effects to properly applied TENS therapy.

Several theories have been developed to explain the neurophysiological mechanisms through which TENS can affect pain perception. The earliest accepted explanation is the gate control theory, first postulated by Melzack and Wall in 1965 (Melzack, R. Wall P. D., "Pain mechanisms: a new theory," Science 150, pp. 971-979, 1965). This theory used data from animal experiments to predict that stimulation of afferent nerves could inhibit transmission from both noxious and nonnoxious inputs. Research with commercially available stimulators has demonstrated that TENS efficacy cannot be explained by the gate control theory alone (Schmidt R. F., "Presynaptic inhibition in the vertebrate central nervous system," Ergebn. Physiol. 63, pp. 20-86, 1971).

More recent studies (Eriksson M. B. E., Sjolund B. H., Nielzen S., "Long term results of peripheral conditioning stimulation as an analgesic measure in chronic pain," Pain 6, pp. 335-347, 1979) have shown that TENS efficacy can be greatly enhanced for some patients by supplementing new stimulation techniques when unsatisfactory results are obtained with conventional stimulation. One popular technique incorporates experience from Chinese electroacupuncture. The discovery that the effects of this technique, as well as those from acupuncture, can be reversed with an opioid antagonist, naloxone hydrochloride (Sjolund B. H., Eriksson M. B. E., "The influence of naloxone on analgesia produced by peripheral conditioning stimulation," Brain Res. 173, pp. 295-301, 1979, and Mayer D. J., Price D. D., Rafii A., "Antagonism of acupuncture analgesia in man by the narcotic atagonic naloxone," Brain Res. 121, pp. 368-372, 1977) suggested the possibility of an endogenous opiate system responsible for pain control. Since 1975, several endogenous, morphine-like peptides have been isolated (Hughes J. et al, "Identification of two related pentapeptides from the brain with potent opiate agonist activity," Nature 258, p. 577, 1975), including endorphins which have been found in numerous locations within the central nervous system (Matsukura S. et al, "The regional distribution of immunoreactive beta-endorphin in the monkey brain," Brain Res. 159, p. 228, 1978).

The above results have led some researchers (Eriksson M. B. E., Sjolund B. H., Nielzen S., "Long term results of peripheral conditioning stimulation as an analgesic measure in chronic pain," Pain 6, pp. 335-347, 1979) to the conclusion that more than one neurophysiological mechanism is involved in modulating pain through transcutaneous stimulation. This theory is supported by clinical studies (Mannheimer J. S., Lampe G. N., "Clinical transcutaneous electrical nerve stimulation," F. A. Davis Company, Philadelphia, pp. 345-348, 1984) that demonstrate the different characteristics shown in Table 1 for conventional and acupuncture-like TENS.

TABLE 1

Characteristics of TENS Modes

| Characteristic | Conventional | Acupuncture-like | Simultaneous Bimodal |
|---|---|---|---|
| Intensity | low | high | combined |
| Rate | high | low | combined |
| Relief Onset | rapid | slow | rapid |
| Relief Duration | short | long | long |
| Accommodation | likely | unlikely | slight accommodation likely |
| Naloxone Reversible Effects | no | yes | reduced effects |

The listed properties for simultaneous bimodal (combined stimulation modes) stimulation assume that conventional and acupuncture-like stimulation use different stimulation mechanisms and that their effects are additive. This assumption's validity has been demonstrated in case studies (Mannheimer J. S., Lampe G. N., "Clinical transcutaneous electrical nerve stimulation," F. A. Davis Company, Philadelphia, p. 431, 1984), but more comprehensive research is needed.

Researchers have found that relevant electrical signal characteristics which must be examined in attempting to treat a painful sensation include the signal waveform, pulse repetition frequency, pulse duration, pulse amplitude and pulse modulation characteristics.

An example of a device which attempts to treat pain by electronic stimulation based on these principles is disclosed by Keller in U.S. Pat. No. 4,210,151. The Keller device employs a scanning oscillator which varies the pulse duration, pulse frequency and pulse amplitude. This repetitive variation of parameters guarantees that, at least for some small portion of the duty cycle, the optimum nerve stimulation conditions are achieved.

Finally, U.S. Pat. No. 4,340,063, issued to Maurer, discloses a nerve stimulation device in which the amplitude of the pulse decreases with a decrease in pulse width along a curve defined by a hyperbolic strength-duration curve for living tissue. The imitation of this particular waveform results in a proportionately greater recruitment of nerve fibers due to the nonlinear relationship between pulse width and threshhold. The foregoing references are included by way of presentation of the background of the invention and do not constitute the inventive concept of the present application.

SUMMARY OF THE INVENTION

The invention is directed to the application of digital electronic techniques to control the pulse width and frequency of a pulsed electrical signal which is applied through electrodes placed in contact with the surface of the skin to stimulate nerves. A potentiometer is adjusted by the patient to control the amplitude of the pulses. The rate and duration of the pulses is controlled digitally and may be determined either by programmed information contained in a nonvolatile memory or by the position of a potentiometer depending upon whether or not the device is in its clinical programming mode.

The intensity of the stimulation is determined both by the amplitude and the duration of the individual pulses, while the pulse rate determines the perceived continuity of the applied stimulation. The output of the device will be applied to the patient's skin through one or two separate channels. By increasing the intensity of the pulses, muscle contraction may also be facilitated.

TENS devices will display the intensity and rate for each channel through a bar graph depicted on a liquid crystal display. The display will indicate modulation changes in both rate and duration as they occur. The condition of the battery will also be continuously monitored, by a comparison of the scaled voltage supplied by the battery while loaded, to a regulated reference supply voltage and when a sufficiently low battery voltage is reached, a warning signal will appear on the liquid crystal display. Muscle stimulation devices will display off time instead of rate in a bar graph since rate is fixed in these devices. This indicator will let the patient know when the next contraction will occur, thereby eliminating the surprise associated with infrequently recurring intense stimulation.

During clinical programming, rate and pulse width are displayed numerically on the liquid crystal display to facilitate clinical adjustment. During patient use, these numeric displays indicate amplitude, to facilitate patient adjustment.

The present invention also contains a microprocessor and memory which will permit diagnostic tests to be performed on both the software and hardware of the present device such that most anomalous conditions will cause a warning signal to appear on the liquid crystal display while simultaneously discontinuing the application of stimulation to the patient.

External devices may be interfaced with the present apparatus by means of a serial communications link to provide a supplemental programming method. The apparatus may be programmed so as to provide fully independent parameters for each channel, including both pulse width and pulse rate. TENS clinical controls also include pulse width or frequency modulation or a combination of both which will modify the pulse width and pulse frequency as determined either by information contained in the nonvolatile memory or from mechanical switches. Modulation depth, which determines the amount of variation in pulse width or pulse frequency either from information in the nonvolatile memory or from a potentiometer, may also be controlled. Similar control will also be available for the modulation rate, which varies the frequency at which modulation occurs. Similar control will also be available for duty cycle which reduces the percentage of intense stimulation during modulation.

Muscle stimulation clinical controls also include stimulation on and off times. Rise time, which is the time required for pulse duration to reach its maximum value, is also clinically adjustable. It will also be possible to select simultaneous or reciprocal stimulation for dual-channel operation. There will also be a clinical control providing a continuous mode which will facilitate selection of rate and duration and to maintain constant pulse parameters while electrode sites for optimum stimulation are being located. The combination of these features will allow an almost infinite number of stimulation algorithms for each independent stimulation channel.

Therefore, according to one aspect of the invention, there is provided an electrical stimulator for use by a human patient, comprising means for generating a pulsed signal, and means for controlling the pulsed signal parameters, wherein a first set of parameters may be adjusted by manipulating operator controls and a second set of parameter values may be adjusted by manipulating programming controls.

According to a further aspect of the invention, there is provided an apparatus as recited above wherein the second set of the pulsed signal parameters include signal modulation amplitude, on time, off time, rise time, signal modulation rate, type of signal modulation, signal pulse width, and signal pulse frequency. The parameter values within the second set of pulsed signal parameters may vary over a sufficiently wide range to permit use of the electrical stimulator as either a transcutaneous electrical nerve stimulator or as a muscle stimulator.

Further, the parameter values within the first set of pulsed signal parameters are confined to values that will be safe to the patient utilizing the stimulator regardless of the patient's manipulation of the operator controls.

Still further, the first set of pulsed signal parameters may be controlled by the patient by relatively elementary manipulation of the operator controls, said manipulation thereby initiating relatively sophisticated pulsed signal behavior, the relatively sophisticated pulsed signal behavior being determined by prior manipulation of the programming controls.

Another feature provided for in one aspect of the invention is for the adjustment of the pulsed signal parameters within the second set, accomplished by means of a plurality of potentiometers, each potentiometer corresponding to a specific pulsed signal parameter, said potentiometers thereby serving as the programming controls.

A further feature provided is an analog to digital interface, the analog and digital interface serving to monitor the condition of the battery, the battery serving as an electrical power source for the electrical stimulator.

DESCRIPTION OF THE PREFERRED EMBODIMENT

Figure 7:
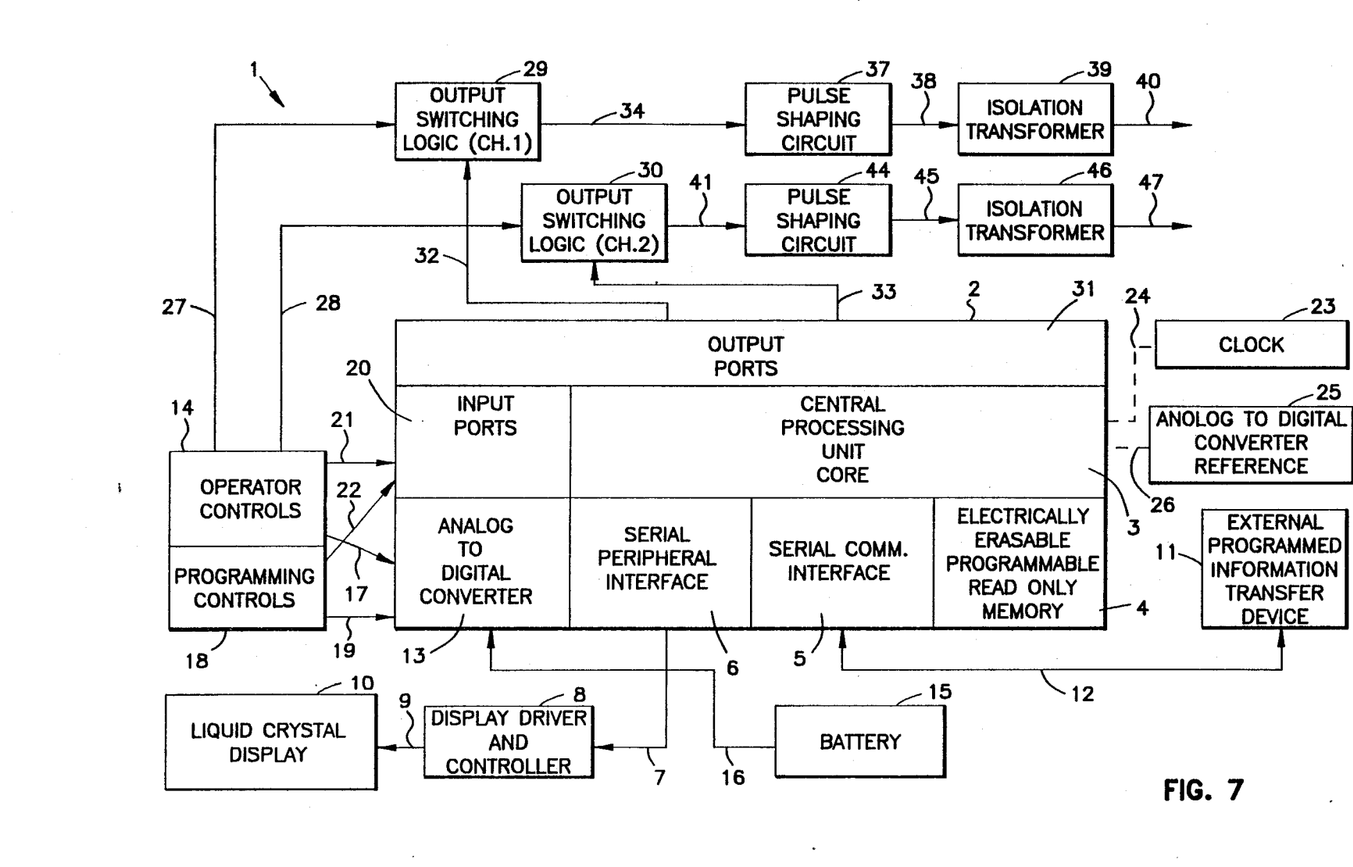
FIG. 7 shows a block diagrammatic version of an illustrated embodiment of the present invention.

FIG. 7 shows generally at 1 a block diagrammatic version of the preferred embodiment of the present invention. The data processing functions of the present invention are performed by single chip microcomputer 2, which preferably is a single integrated circuit chip utilizing high speed complimentary metal oxide semiconductor technology so as to provide low power consumption, immunity to noise and high speed operation. In the preferred embodiment, microcomputer 2 is a semiconductor manufactured by Motorola, Incorporated, part number MC68HC11A8. The central processing unit functions are carried out at core 3 the central processing unit accommodating a total of seven registers, including two 8-bit accumulators, two index registers, a stack pointer, a program counter, and a condition code register.

The two accumulators, referred to as accumulator A and accumulator B, are used to store the results of arithmetic operations or data manipulations. The two accumulators can be combined into a single 16-bit accumulator.

The two index registers, X and Y, each create a 16-bit indexing value which, when combined with program instructions, creates an effective address.

The stack pointer is a 16-bit register containing the address of the next open location on the stack. The stack protocol is a series of last in, first out, read/write registers which permit the storage of data during interrupts and subroutine calls.

The program counter is a 16-bit register containing the address of the next instruction scheduled for execution. Finally, the condition code register is an 8-bit register in which each bit indicates the results of the instruction most recently executed. Each of these bits can be most easily tested by a program, the results of which can be used to initiate a specific action.

Clinically programmed parameters are stored in electrically erasable programmable read-only memory (EEPROM) 4. The EEPROM has a memory capacity of 512 bytes. The programming and erasure of the EEPROM memory is controlled by an 8-bit programming control register. Clinical programming will normally be accomplished through use of an external control push button. A depressed push button will activate clinical controls. Releasing the push button inactivates clinical controls and initiates storage of the most recent clinical parameters in EEPROM.

Clinically programmed parameters may also be modified and introduced to EEPROM 4 via serial communications interface 5. The serial communications interface contains two serial communications control registers, a serial communication data register and a serial communication status register. One of the serial communications control registers permits selection of the data word length, while the other serial communications control register provides control bits which individually enable or disable the transmitter or receiver. There is also a baud rate register to permit the user to select different baud rates which may be used as the rate control for the transmitter and receiver. Data transmission begins by writing to the serial communications data register. The serial communication status register provides input to the interrupt logic circuits for generation of the serial communications interface system interrupt. An external information transfer device 11, such as a personal computer, may be used to transfer programmed information to or from the serial communications interface 5 along signal path 12. The transferred information may also take the form of real time telemetered data.

Access to external display devices may be accomplished through serial peripheral interface 6. Serial peripheral interface 6 is a synchronous interface, integrated into the basic microcomputer integrated circuit 2, thereby allowing the interconnection of peripheral equipment. The serial peripheral interface 6 contains a control register, status register, and data storage register. In the present embodiment, the output of serial peripheral interface 6 travels along signal flow path 7 until reaching display driver and controller 8. The output of the display driver and controller may follow signal path 9 until reaching a suitable display 10, such as a liquid crystal display.

Some information supplied to integrated circuit 2 is necessarily in analog form, and therefore must be converted into a digital form in order to undergo further processing by the integrated circuitry. Therefore, integrated /circuit 2 includes an eight channel, multiplexed input, successive approximation analog to digital converter 13. Examples of analog information include battery instantaneous voltage supplied by battery 15, appropriately scaled by diodes 71, 73, 188, and resistors 184, 185, which is then transmitted to converter 13 where it is compared to the reference voltage at 48 which is supplied by voltage regulator 72. Other examples include along signal path 16, accomplished by appropriate connection of a control push-button switch (not shown) to pin 58 (PA7) of four pin jack 53 and to ground connection 54. The other terminals of jack 53 are connected to serial communication input/output ports PD0 and PD1 (pins 57 and 56, respectively) on chip 2 certain operator controls 14 (such as amplitude), and the information flowing along signal path 17 to converter 13. Also, some clinical programming controls 18 (such as modulation depth) convey information to converter 13 along signal path 19.

Other information is already in a digitized state, and thus can flow directly to input ports 20, such information traveling from operator controls 14 along signal path 21 or emanating from clinical programming controls 18 along signal path 22.

The rate at which any of the various data being transmitted to chip 2 is processed, or any internal arithmetic operation is performed, is entirely dependent on the clock frequency transmitted to central processing unit core 3 by clock 23 along signal path 24. Actually, integrated circuit 2 contains internal clock generator circuitry and requires only an external interface with either a crystal or a CMOS compatible clock. Similarly, the analog to digital converter 13 requires an analog to digital converter reference 25 which provides a direct current voltage level along current path 26 to central processing unit core 3.

Integrated circuit 2 includes forty input/output pins organized as five 8-bit ports. All of these pins serve multiple functions depending on the operating mode and the status of several internal control registers. Several of the ports may be termed as "general purpose" insofar as the direction of data may vary depending on the status of a bit in the corresponding data direction register. Other ports have fixed data directions and do not need data direction registers. In the present invention, the ultimate output of the stimulator device 1 is supplied to the patient in the form of two discrete outputs, or channels, which for convenience will be referred to as channels A and B, respectively. Thus, signal path 27 corresponds to channel A, while signal path 28 corresponds to channel B. Signal path 27 flows to output switching logic 29, corresponding to channel A, while signal path 28 flows to output switching logic 30, corresponding to channel B.

Output ports 31 are also interconnected to the output switching logic. Specifically, signal path 32 leads from output port 31 to output switching logic 29, while signal path 33 leads from output port 31 to output switching logic 30. The output ports provide a signal to the output switching logic so as to transmit and interrupt the amplified signal coming from the operator controls, thereby providing pulse width and frequency control.

Referring now particularly to the signal flowing through channel A, the signal follows signal path 34 from output switching logic 29. The signal then follows path 36 and is processed by pulse shaping circuit 37. The shaped pulse follows signal path 38 and passes through isolation transformer 39, the output of the transformer following signal path 40 until reaching a suitable electrode (not shown) which may be applied directly to the patient's skin, usually through a transmission media such as conductive gel.

The signal path followed by the channel B pulse is substantially identical, the pulse leaving output switching logic 30 along signal path 41. The signal continues along signal path 43 through pulse shaping circuit 44, continuing along signal path 45 through isolation transformer 46 and traveling along signal path 47 until reaching an electrode.

Figure 6A:
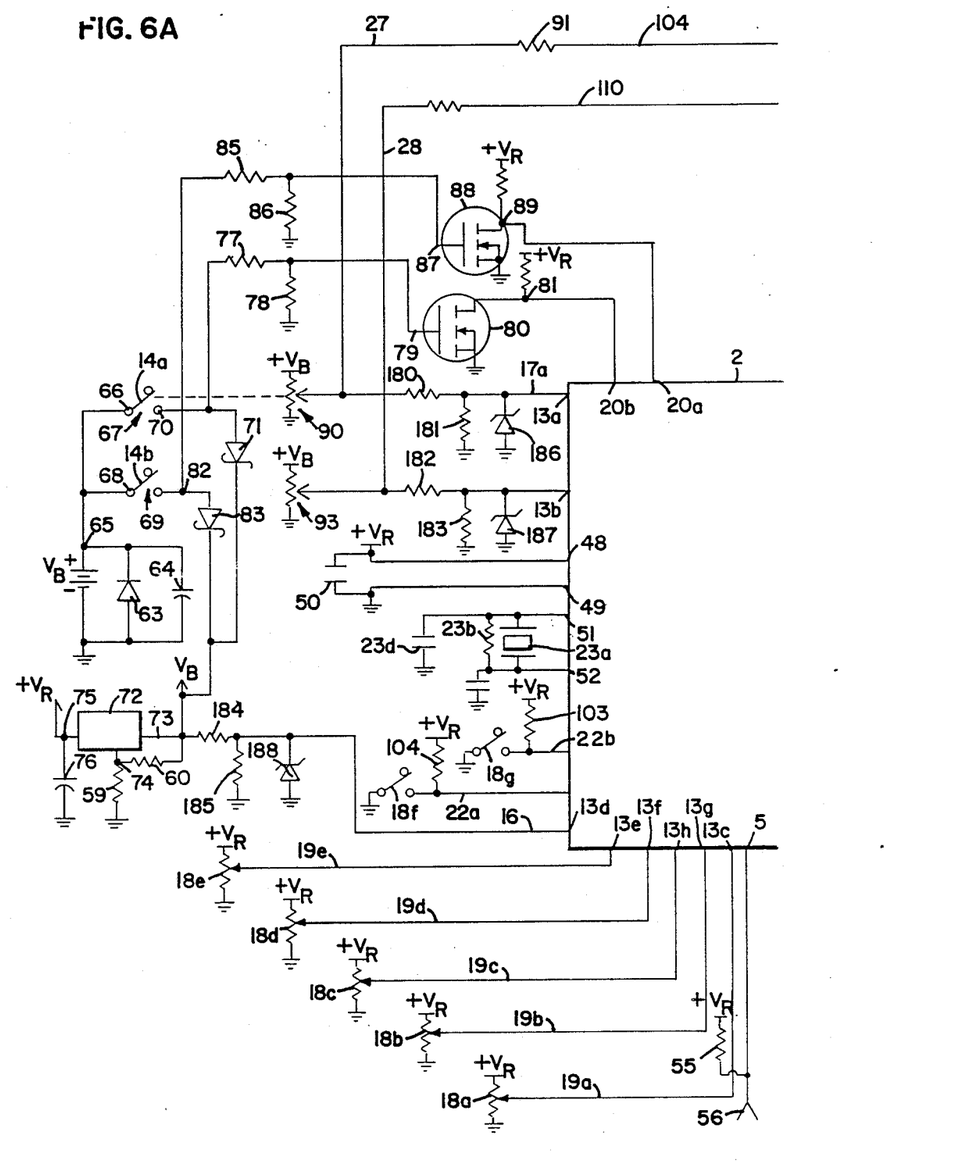
FIGS. 6A and 6B, when appropriately joined together, depict a circuit schematic of a preferred embodiment of the present invention.
Figure 6B:
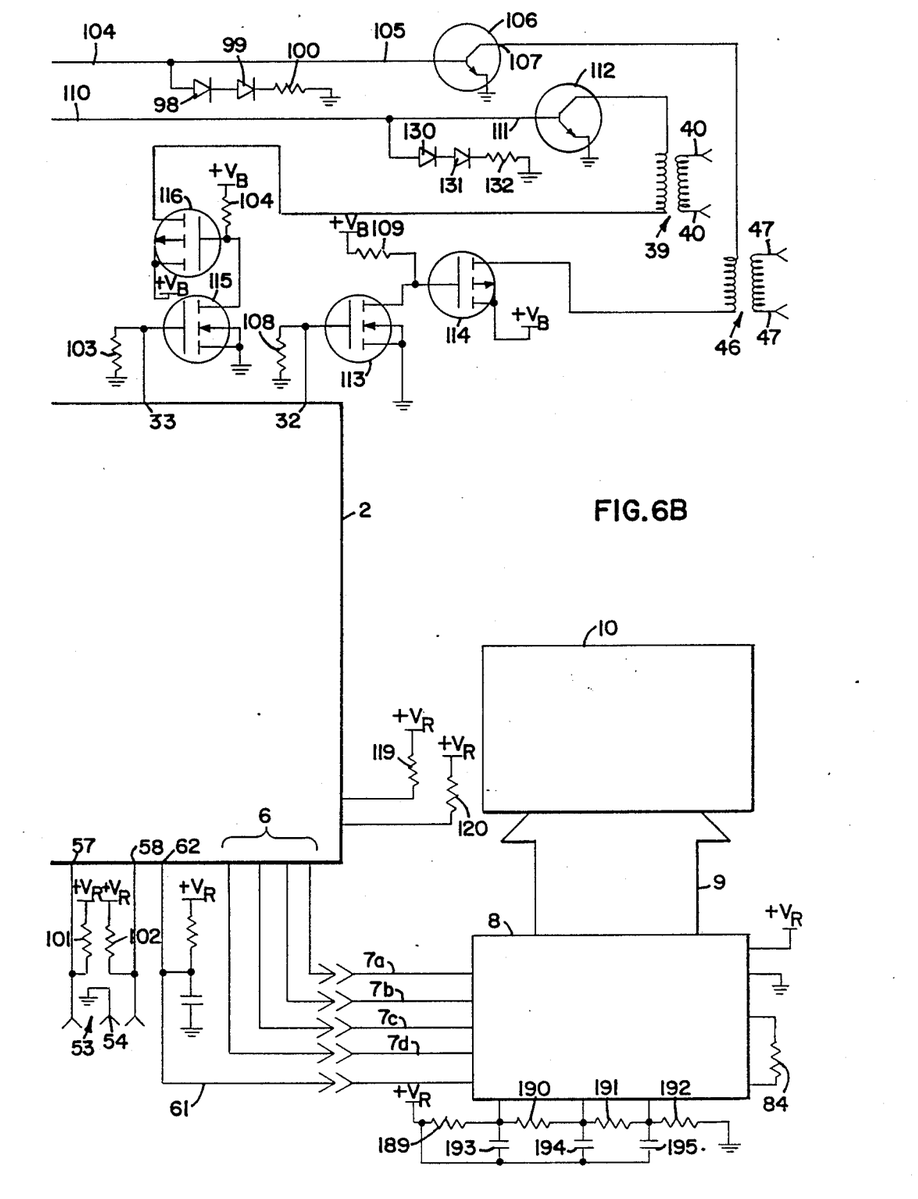

The main functional element of the present invention is integrated circuit 2, which corresponds to integrated circuit 2 as shown in FIG. 6. As stated earlier, integrated circuit 2 is preferably of the type manufactured by Motorola, Incorporated, bearing part number MC68HC11. This particular integrated circuit is characterized by having 8,000 8-bit bytes of read only memory, 512 bytes of non-volatile electrically erasable, programmable read only memory, 256 bytes of random access memory, an enhanced 16-bit timer system, a pulse accumulator circuit, a serial communications interface, a serial peripheral interface, and an 8 channel, 8-bit analog to digital converter. Power (VDD), provided by voltage regulator 72, is supplied to integrated circuit 2 via pin 48. The input voltage is typically a positive five volts, the ground (VSS) reference being provided at pin 49. Capacitor 50 is used to provide some filtering to the input voltage VDD.

The external clock circuitry depicted at 23 at FIG. 6 includes crystal 23a, parallel resistor 23b and capacitors 23d and 23c. The external crystal circuitry is attached to integrated circuit 2 at pins 51 (EXTAL) and 52 (XTAL).

The external programming of the device may be accomplished by appropriate connection of a control pus-button switch (not-shown) to pin 58 (PA7) of four pin jack 53 and to ground connection 54. The other terminals of jack 53 are connected to serial connection input/output ports PD0 and PD1 (pins 57 and 56, respectively) on chip 2. Pull-up resistors 101, 55, and 102 lead from pins 57, 56, and 58, respectively, to an appropriate five-volt power source.

As shown in FIG. 6, serial peripheral interface 6 is connected to display driver and controller 8 which controls liquid crystal display 10 through signal path 9. The signal path 7 as shown in FIG. 7 corresponds to the four signal paths 7a, 7b, 7c and 7d as shown in FIG. 6B. Additionally, a reset line 61 leads from integrated circuit 2 to display driver and controller 8. The reset line 61 is connected to active low by directional control pin 62, which is used as an input to initialize integrated circuit 2 to a known startup state. (The capacitor at this port provides momentary low logic which resets both integrated circuit 2 and controller 8. The resistor charges the capacitor, which allows normal processing to begin.) Diode 63 is used to prevent damage from backwards installation of battery 15. Capacitor 64 permits battery 15 to provide the high current surges necessary for the stimulator output circuit and provides some filtering for the 9 volt supply 15.

Operating voltage for the entire device 1 is provided by battery 15, the battery being in parallel with diode 63 and capacitor 64. The positive terminal 65 of battery 15 is connected directly to the center post 66 of switch 67 (corresponding to channel 1) and the center post 68 of switch 69 (corresponding to channel 2). In FIG. 6, both switches 67 and 69 are shown in the "off" position.

When switch 67 is activated, thereby activating channel 1, center post 66 is placed in electrical connection with "on" position 70, thereby permitting the positive voltage emanating from battery 15 to travel through schottky diode 71 to voltage regulator 72. Voltage regulator 72 has a first terminal 73 which is connected to the battery 15 voltage (nine volts), a second terminal 74 which allows output adjustment by resistors 59 and 60 which are selected to provide a nominal output of +5 volts, and a third terminal 75 which supplies the desired output of +5 volts. The output voltage appearing at terminal 75 is filtered by capacitor 76. Resistors 77 and 78 are used to properly bias and turn on FET 80. A logic "0" at terminal 20b (PA0) resulting from this condition indicates the active status of switch 67 to the microcomputer 2.

Similarly, when switch 69 is "on," center terminal 68 is connected to terminal 82, thereby permitting current from battery 15 to pass through schottky diode 83, thus activating regulator 72. The associated channel 2 circuitry is similar in operation to that just described for channel 1, with resistors 85 and 86 biasing FET 88, a logic "0" at terminal 20a (PA1) indicates the active status of switch 69 to the microcomputer 2.

When switch 67 is turned "on," potentiometer 90 is also activated, potentiometer 90 controlling the voltage reaching input port 13a (PE7) of the analog to digital converter portion of integrated circuit 2, the signal path 17a corresponding to one of two operator control signal paths shown as single signal path 17 in FIG. 7. Similarly, signal path 27 corresponds to the channel A signal path from signal path 27 as shown in FIG. 7, the current flowing through signal path 27 subsequently passing through resistor 91.

The voltage at the base 105 of transistor 106 determines the level of the constant current sink provided by the transistor 106, along with diodes 98 and 99 and resistor 100 which are also connected to base 105. Output port 32 generates a signal which applies power to the isolation transformer 46, through switching field effect transistors 113 and 114. The timing of the output switching logic determines the frequency and duration of the pulse train at the isolation transformer 46, the output of which follows signal path 47 through suitable electrodes (not shown). Pulse amplitude is constant current over the range of output impedance from approximately 10 ohms–5000 ohms as determined by the voltage at the base 105 of transistor 106.

Channel B operates in a similar fashion, with potentiometer 93 being co-located with channel B switch 68 such that the voltage appears across potentiometer 93, potentiometer 93 leading to analog to digital converter port 13b and having an output corresponding to signal path 28 shown in FIG. 6. The voltage at the base 111 of transistor 112 determines the level of the constant current sink afforded by transistor 112 along with diodes 130 and 131 and resistor 132 which are also connected to base 111. Output port 33 generates a signal which applies power to the isolation transformer 39 through switching field effect transistors 115 and 116.

Diodes 98, 99, 130 and 131, and resistors 100 and 132 provide proper biasing for the constant current sourcing provided by transistors 106 and 112. They also provide temperature independence. For further information, reference *Integrated Electronics*, by Millman and Halkais, McGraw-Hill, pp. 508–509.

Pull-up and pull-down resistors 103, 104, 108 and 109 define the inactive state (off) of switching FETS 113 through 116.

Resistors 180-185 are used to scale parameters ranging from 0 to +9 Volts D.C. to the 0 to +5 volts range required by the microcomputer's A/D converter. Zener diodes 186-188 clamp the maximum voltage at terminals 13a, 13b, and 13d to a nominal maximum of 4.7 volts D.C. This protects microcomputer 2 from the possibility of caused by input voltages in excess of the +5 volt VDD supply at 48.

Pull-up resistors 103 and 104 provide a logic high to ports 22b and 22a respectively, when switches 18g and 18f are inactive (open).

Resistor 108 and capacitor 109 provide the momentary low needed to reset the system as mentioned above.

Resistors 189-192 and capacitors 193-195 provide the proper bias voltages to drive the multiplexed custom liquid crystal display 10.

Resistor 84 implements the clock oscillator circuitry which synchronizes the internal logic and data flow of display controller 8.

Pull-up resistors 119 and 120 prohibit external resets at the XIRQ and IRQ interrupt pins.

Figure 1:
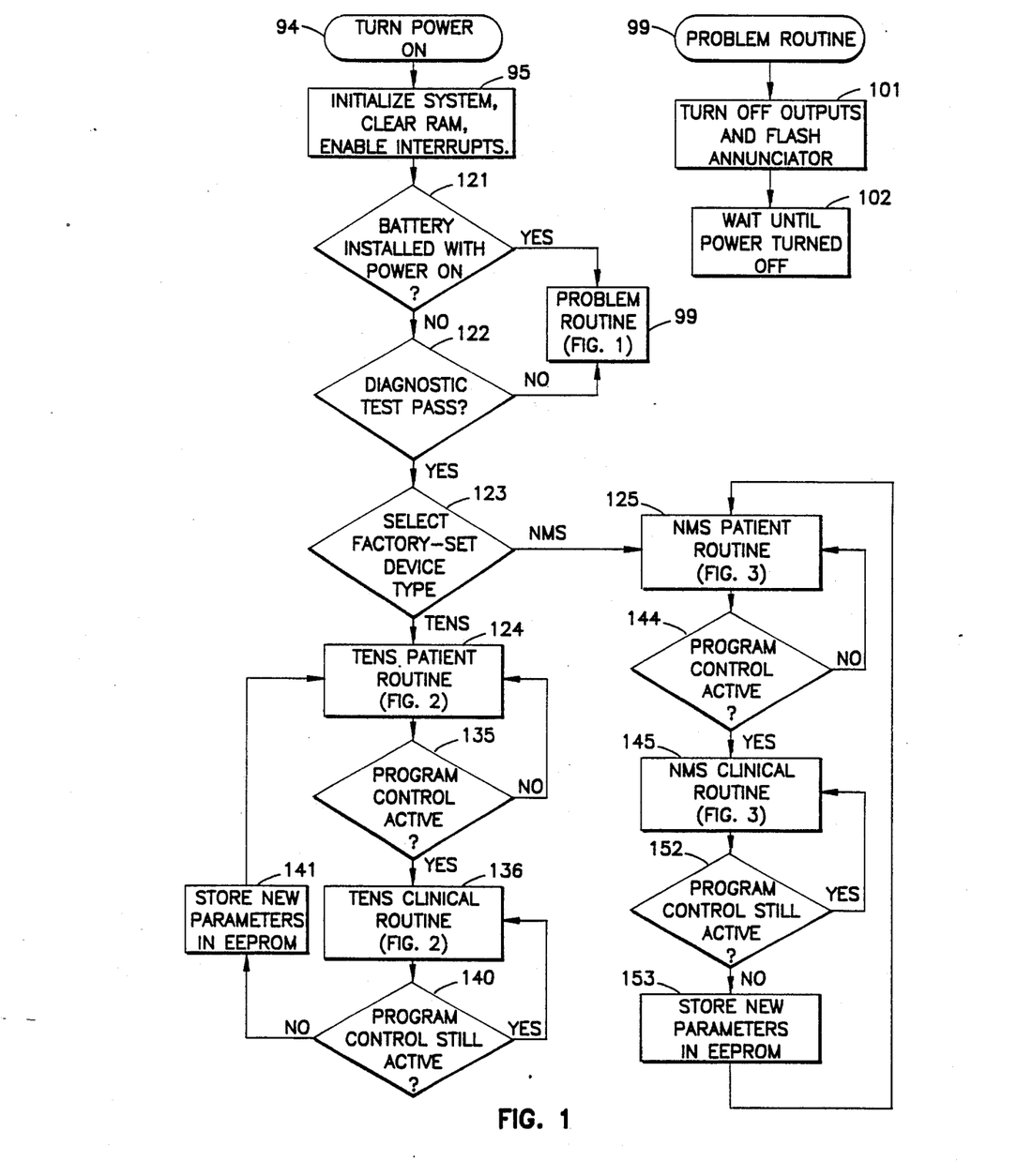
FIGS. 1-5 are a series of flow charts showing the programming steps performed during utilization of the present invention.

FIG. 1 is a flow chart illustrating the steps performed by microprocessor 2 during the operation of the present invention. The first step 94 is to initialize certain values, such as the default locations of random access memory and internal registers within the microcomputer memory map. These values are entered automatically when power is applied to the microcomputer. The next step 95 involves selecting options and configuring the microcomputer in the desired mode. This involves the selection and initialization of the various hardware and software options to be used, defining certain ports as input or output, initializing output logic states, clearing all working RAM bytes, defining the stack location and enabling interrupts.

The next step 121 requires reading the status of channels A and B (either on or off). If both channels have the same status, the programming step diverts to problem subroutine 99, which affirmatively turns off both outputs of channel A and B at step 101, and causes an annunciator to flash. All other display information is suppressed at step 102 and other activities cease until the power is finally shut off.

Returning to step 121, if only one channel is on, the microcomputer samples that channel's amplitude through the appropriate A/D port. If the amplitude value obtained is too high, control reverts to problem subroutine 99 already described, problem subroutine 99 indicating to the user an excessive amplitude condition which was most likely caused by installation of the power source .(battery) while the amplitude control was left turned up, or by an interruption of power due to a fault in the power supply circuitry.

If the channel amplitude value read at step 121 is acceptable, control returns to logical interrogation step 122. This step performs certain diagnostic tests on RAM, ROM, EEPROM and various hardware accessible to the microcomputer. If the results of these tests are not acceptable, control reverts to problem subroutine 99, already described.

If all diagnostic tests are performed satisfactorily, control proceeds to logical interrogation step 123 which tests the factory-set status port to determine if the device is configured as a TENS or NMS unit. Control then reverts to the routine for the appropriate device type.

Figure 2:
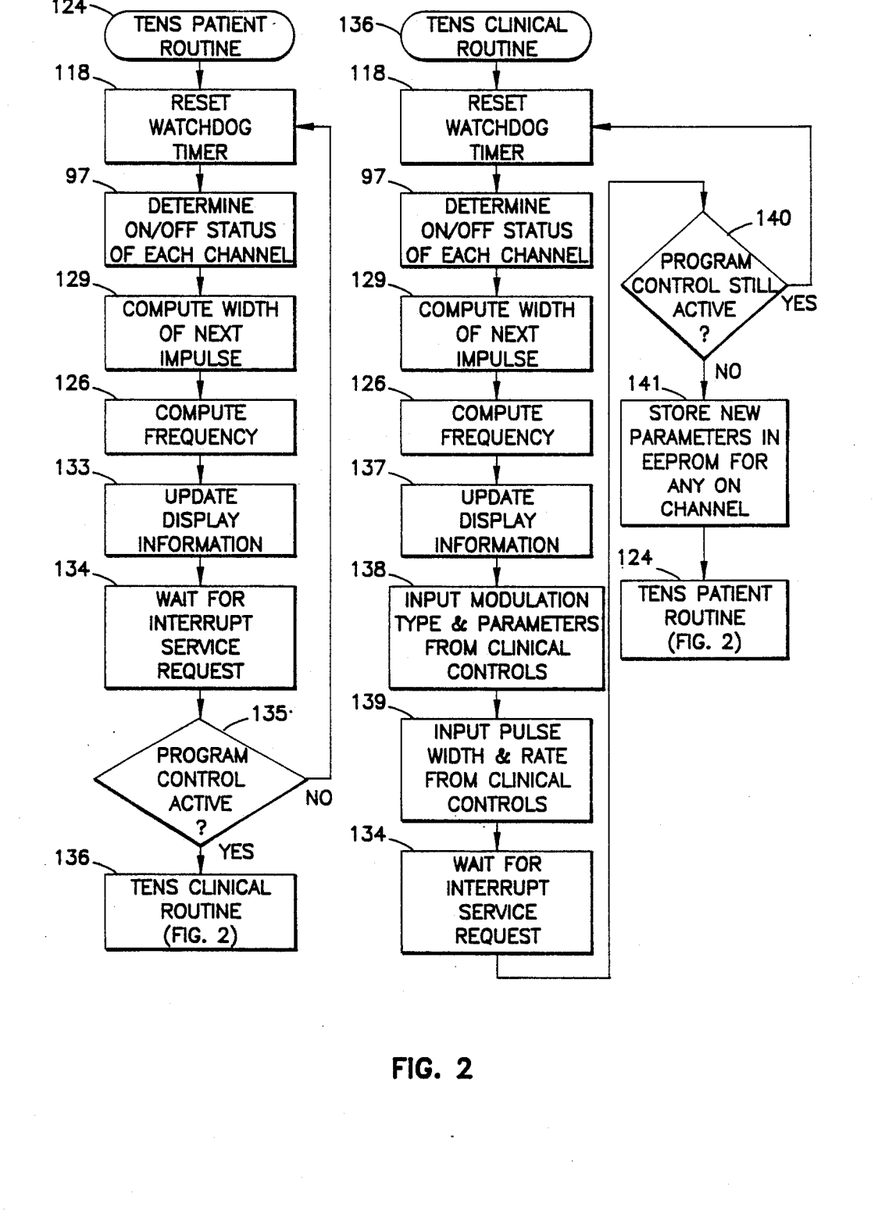

FIG. 2 is a flow diagram illustrating the continuous cycle of steps taken by microcomputer 2 when configured as a TENS device. The first step 118 of this loop is to reset the computer watchdog t is an internal protection feature of the MC68HC11 microcomputer. If this timer is not reset within a specific time, interrupt 165 as shown on FIG. 5 will be automatically generated by the microcomputer.

The next logical step 97 is to determine the on/off status of each channel from the logic state at ports 20a and 20b. This information is used both for output processing and display.

Logical step 129 uses the nominal pulse width values stored in EEPROM to compute a 16 bit value which is used by the OC1 timer (discussed later) to initialize the OC2 and OC3 counters (discussed later) for pulse width timing. If either channel is configured for pulse width modulation by the status registers in EEPROM, the pulse width value calculated above for that channel may be reduced in proportion with the modulation depth value (also stored in EEPROM) for that channel, depending upon the status of the modulation rate timer associated with that channel.

Logical step 126 uses the nominal frequency parameters stored in EEPROM to derive 8-bit counter values to be used in the OC1 timer (discussed later) to establish frequency timing for each channel. If either channel is configured for rate modulation by the status registers in EEPROM, the frequency value calculated for that channel may be increased (frequency reduced) in proportion to the modulation depth parameter (also stored in EEPROM) for that channel, depending on the status of the modulation rate timer associated with that channel.

The next logical step 133 requires a sample of each active channel's amplitude through A/D ports 13a and 13b. The samples thus obtained are scaled to values between 1 and 99 inclusive, for numeric amplitude displays, and are also compared with pulse width modulation status and depths for the bar graph intensity displays. The frequency parameters are then compared with the rate modulation status and depths for the bar graph rate displays. Alarm and operational status is then polled for selection of annunciators to be displayed. The information thus obtained is then fed to display controller 8 through the serial peripheral interface 6. Display controller 8 then uses this information to appropriately drive the custom liquid crystal display 10.

The next logical step 134 uses the microcomputer's WAIT instruction to put the microcomputer in a low-power consumption mode. An interrupt request is required to exit this mode.

The next logical interrogation step 135, as shown in both FIGS. 1 and 2, samples the logical status of port 58 to see if the external program control switch is connected and active. In some models this test may be replaced by a test that detects an active serial communication interface at port 57. A positive result of the above test leads to a transfer of control to the TENS clinical routine. A negative result of the above test reverts control to the beginning of the patient routine loop at step 118.

Logical steps 118 through 126 in the TENS clinical routine 136 of FIG. 2 are identical to the same-numbered steps of the TENS patient routine 124 already discussed and will not be elaborated on further.

In logical step 137, the bar graph and annunciator information is obtained in a manner identical to that already discussed for step 133. The actual frequency and pulse width of the pulse train is used the numeric displays in step 137 rather than amplitude as in step 133. Display information is then transmitted to display controller 8 through the serial peripheral interface 6 in a manner identical to that discussed for step 133.

In logical step 138, the modulation status as transmitted through signal path 22 in FIG. 6 is read. Next, the position of the clinical controls, modulation depth 18e, modulation rate 18d, and duty cycle 18c is read by converting the associated potentiometer voltage to digital information through the microcomputer's A/D converter. The corresponding modulation parameters are then updated. As mentioned previously, clinical control information may alternatively be supplied through the serial communication interface 5.

In logical step 139, the nominal rate and pulse width are read from clinical controls 18a and 18b respectively, by converting the voltage supplied by the associated potentiometers to digital form through the microcomputer's A/D converter. These parameters, along with the modulation parameters obtained in step 138, will be used in the next loop iteration at steps 129 and 126 to determine the actual frequency and duration of the output pulse train. Rate and pulse width information also may be alternately obtained from external devices through serial communication interface 5, as previously discussed.

Logical step 134 is identical to step 134 in the TENS patient routine 124 already discussed.

In logical interrogation step 140, the status of the program control switch is read as in step 135 of patient routine 124. An active status indication results in control continuing through the clinical loop at step 118. Inactive status reverts control to logical step 141 in which the latest clinical parameters are written to the non-volatile EEPROM for future reference. Processing then continues in the TENS patient routine 124.

Figure 3:
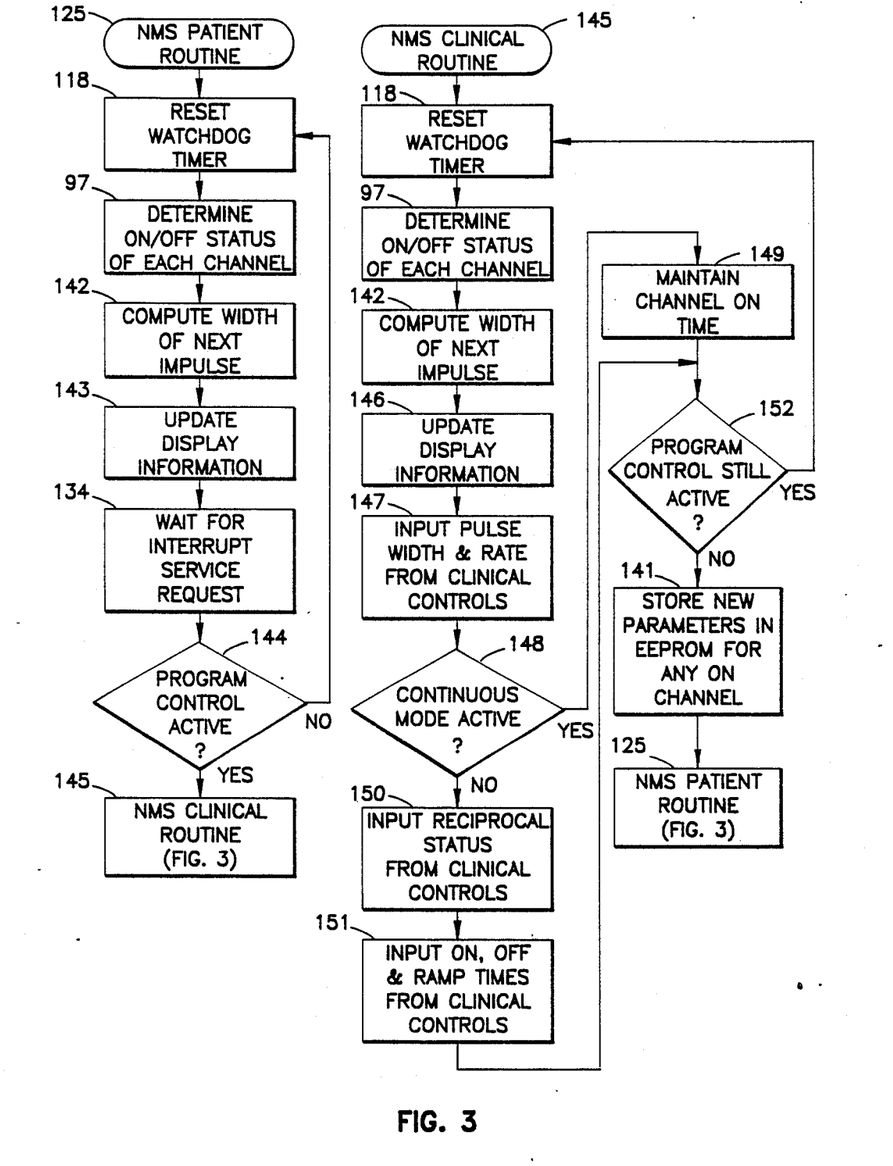

The NMS patient routine 125 of FIG. 3 is entered if the microcomputer finds itself configured as an NMS device in logical interrogation step 123 of FIG. 1.

Logical steps 118 and 97 of the NMS patient routine are identical to the same-numbered steps in the TENS routines of FIG. 2 already discussed.

The next logical step 142 uses nominal pulse width values stored in EEPROM to compute a 16-bit value which is used by the OC1 timer (discussed later) to initialize the OC2 and OC3 counters (discussed later) for pulse width timing. The values calculated above may be reduced (possibly to zero) depending upon the status of the rise, fall, and off-time counters (discussed later) for the channels in question.

Logical step 143 requires a sample of each active channel's amplitude through A/D converter ports 13a and 13b. The samples thus obtained are scaled to values between 1 and 99 inclusive, for the numeric amplitude displays, and if the output is active for any channel, the fraction of actual pulse duration to nominal pulse duration for that channel is compared to the amplitude sample obtained previously for the bar graph intensity display for that channel. If any channel's off timer is active, the fraction of actual off time left to nominal off time (from EEPROM stored values) is displayed in bar graph form on the bar graph used by TENS devices for rate display for the given channel. Alarm and operational status is then polled for selection of annunciators to be displayed. The information thus obtained is transmitted to the display control through the serial peripheral interface 6 as discussed for step 133 of the TENS Patient routine in FIG. 2.

Logical interrogation step 144 tests for an active program control switch in the same manner as in step 135 of the TENS patient routine. A negative result allows processing to continue through the NMS patient loop at step 118. A positive result reverts control to the NMS clinical routine 145 of FIG. 3.

Steps 118, 97, and 142 of the NMS clinical routine 145 in FIG. 3 are identical to the same-numbered steps in the NMS patient routine 125.

In logical step 146, the bar graph and annunciator information is obtained in a manner identical to that already discussed for step 143 of the NMS patient routine 125. The actual frequency and pulse width of the pulse train is used for the numeric displays in step 146 rather than amplitude as in step 143. Display information is then transmitted to display controller 8 as discussed in step 133 of the TENS patient routine 124.

In logical step 147, the nominal rate and pulse width are read from clinical controls 18a and 18b respectively, by converting the voltage supplied by the associated potentiometers to digital form through the A/D converter. The rate information is used by the OC1 timer (discussed later) for frequency timing while the pulse width information is used together with rise, fall, and off-time values in the next loop iteration at step 142 to determine the actual pulse width of the output pulse train. Rate and pulse width may alternatively be obtained from the serial communication interface 5, as previously discussed.

Logical interrogation step 148 tests the logical status of clinical control 18g. An active (low) result transfers control to logical step 149, which sets a flag that keeps the on timer maintained for any active channel. This feature is allowed only during clinical programming to assist clinicians in selecting rate and pulse width and electrode placement. The continuous mode discussed above may alternately be activated by an appropriate instruction received through the serial communication interface 5 from an external device.

If switch 18g is found inactive (high), control proceeds to logical step 150 which tests the logical status of clinical control 18f. This control determines how channels A and B are to be synchronized when both channels are operated simultaneously. They may either be synchronized to rise and fall simultaneously (synchronous operation) or channel B may rise at the beginning of channel A's fall (reciprocal operation), depending on the position of control 18f. The synchronizing action is done in the OC1 timer (discussed later). This clinical control may also be alternatively selected by an external device through the serial communications interface 5.

In logical step 151, the position of the clinical controls (rise time 18e, on time 18d, and off time 18c) is read by converting the associated potentiometer voltage to digital information through the microcomputer's A/D converter. The corresponding timing, parameters are then updated for future use in the OC1 timer (discussed later). This information may also be received from an external device through the serial communication interface 5.

Control proceeds from both steps 149 and 151 to logical interrogation step 152 which tests the status of the external program control switch in a manner similar to step 144 of the NMS patient routine 125. If the control is found in the active state, NMS clinical loop processing continues at step 118.

A result indicating inactive program control switch status at step 152 diverts control to logical step 153 in which the latest clinical parameters are written to the nonvolatile EEPROM for future reference. Stored parameters include pulse width and rate from step 147, reciprocal status from step 150, and ramp time, on time, and off time from step 151. Processing then continues in the NMS patient routine 125.

Figure 4:
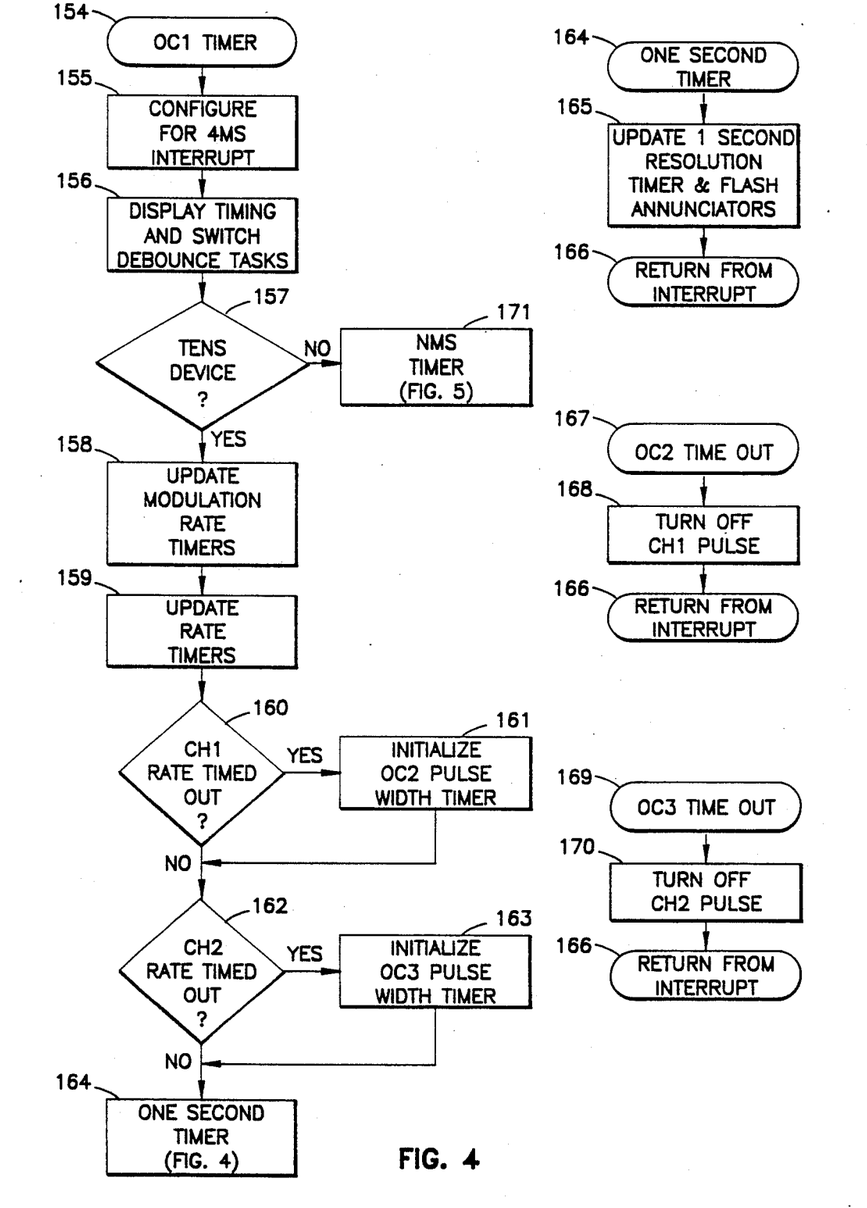

The OC1 timer 154 of FIG. 4 is entered every 0.004 seconds by an internally generated microcomputer interrupt sequence. Logical step 155 performs the administrative steps necessary to prepare for the next four millisecond interrupt.

The next logical step 156 accomplishes switch debouncing which prevents reaction to anomalies in switching logic and controls the timing of display updates and serial transmission to display controller 8.

Logical interrogation step 157 tests the device status in the same manner as step 123 discussed previously. The result of step 157 determines whether processing will divert to the NMS timer 171 or continue at step 158 for TENS devices.

Logical step 158 updates the TENS modulation rate timers which control the frequency of modulation and sets flags accordingly which are used by steps 126 and 129 of the TENS patient and clinical routines to determine if modulation should affect the calculated rate and/or pulse width.

At logical step 159, the rate (frequency) timers for each channel are updated (decremented by 1). Logical interrogation step 160 tests to see if channel A's rate timer is timed out (decremented to 0). If the channel A rate is timed out, logical step 161 first re-starts the rate timer with the frequency information obtained in steps 126 of the main TENS loops. Step 161 then initiates an output pulse by raising the output port and initializing the OC2 pulse timer (discussed later) with the pulse width information obtained in steps 129 of the main TENS loops. Steps 162 and 163 test for rate time out and upon time out initiate an output pulse for channel B in the same manner as steps 160 and 161 for channel A. The OC3 pulse timer (discussed later) is used for timing channel B pulses identically to the OC2 pulse timer for channel A.

Processing next proceeds to the one second timer 164. If one second has not passed at this point, the interrupt is exited at step 166. Logical step 165 is entered upon a one-second pass through the OC1 timer loop. In this step, any timer in which one second resolution is adequate (such as a timer which measures the time spent in clinical programming) is updated and a flag is toggled which causes flashing of certain annunciators. The interrupt is then exited at step 166, which returns control to the routine that was interrupted at the point of interruption.

The OC2 timer interrupt 167 is initiated automatically upon time out of the OC2 timer, which is started at step 161 of the OC1 timer (154). The only action taken in this routine is to terminate the channel A pulse at step 168. The OC2 timer is exited at step 166 in the same manner as the OC1 timer at step 166.

The OC3 timer interrupt 169 performs the same function of terminating the channel B output pulse as the OC2 timer for channel A and terminates in the same manner at step 166.

The NMS timer 171 (FIG. 5) is entered if the microcomputer finds itself configured as an NMS device at step 157 of the OC1 timer 154.

Figure 5:
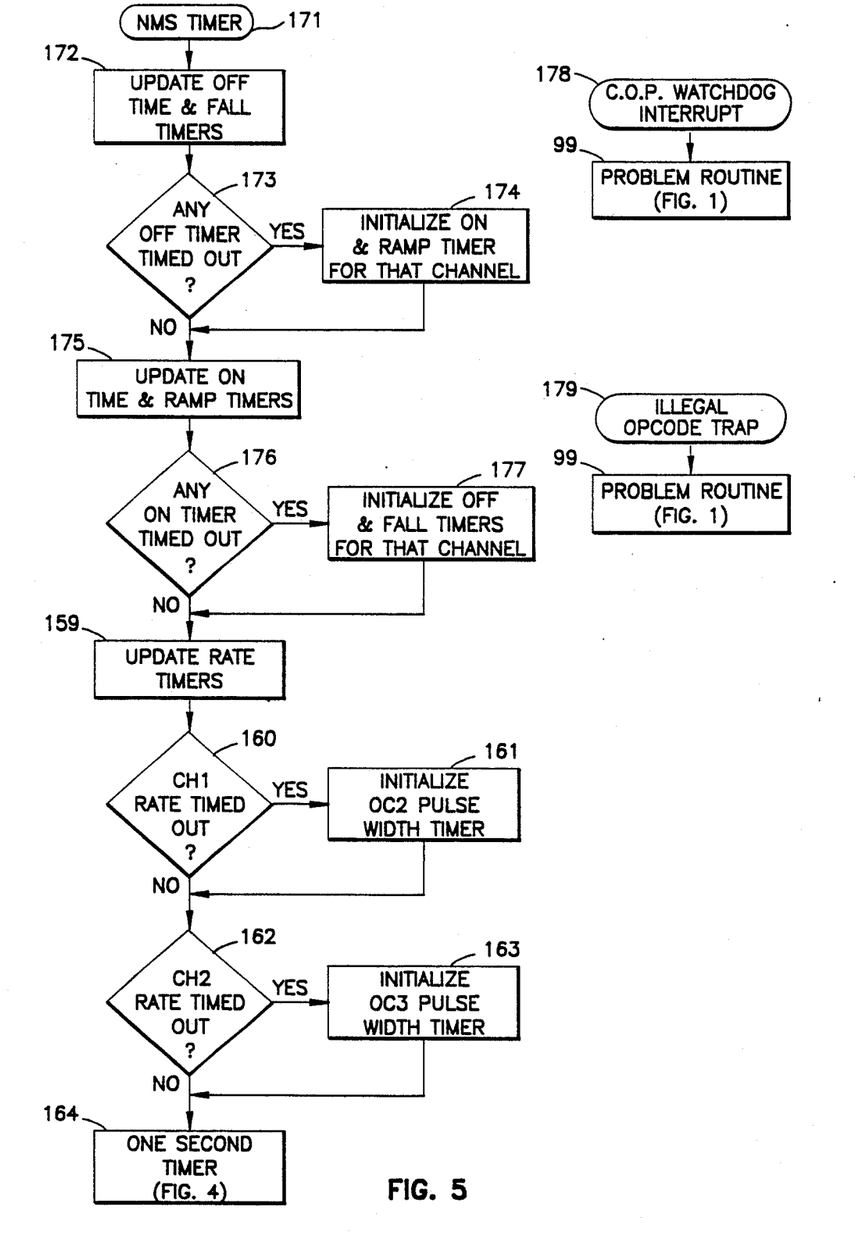

At logical step 172, the off and fall timers of each active channel are updated if they are found to be active (non-zero).

Logical interrogation step 173 tests to see if either off timer was decremented to zero at step 172. If either off timer has timed out as described above, the on and ramp timers for that channel are initialized in step 174 with information from EEPROM if the device is operating in the NMS patient loop 125 or from information obtained at step 151 if the device is being clinically programmed in routine 145

In the next logical step 175, the on and ramp timers of each active channel are updated if they are found to be active (non-zero).

Logical interrogation step 176 tests to see if either on timer was decremented to zero at step 175. If either on timer has timed out as described above, the off timer for that channel is initialized with information from EEPROM if the device has been operating in the NMS patient loop 125 or from information obtained at step 151 if the device is being clinically programmed in routine 145. When an on timer is found timed out in step 176, the fall timer for that channel is initialized with a fixed value corresponding to ½ second in step 177.

Steps 159 through 164 of the NMS timer 171 are identical to the same numbered steps in the OC1 timer 154 already discussed for TENS devices.

If the Computer Operating Properly (COP) watchdog timer is not reset by steps 118 in each main loop within a specified time, the microcomputer automatically generates interrupt 178 which then transfers control to the problem routine 99 to assure safety and notify the user.

If the microcomputer retrieves an instruction not in its repertoire, it will automatically generate interrupt 179 which also transfers control to problem routine 99.

TABLE 2

| Active Components | | |
|---|---|---|
| Name | Component # | MFG. Designation |
| Microcomputer | 2 | Motorola 68HC11A8 |
| Display Controller | 8 | N.E.C. UPD 7225 |
| Regulator, adjustable | 72 | National LM317LZ |
| FET, N-channel switching | 80, 88, 113, 115 | Siliconix BS 170 (or equiv.) |
| FET,P-channel switching | 114, 116 | Siliconix VPO 300 L (or equiv.) |
| Transistor, general purpose | 106, 112 | Motorola 2N2222 (or equiv.) |

I claim:

1. An electrical stimulator for use by a human patient, comprising:
   (a) means for generating a pulsed signal, said pulsed signal having parameters including an amplitude, a pulse width and a frequency, the parameters having values;
(b) means, cooperatively connected to said generating means, for controlling the parameters of said pulsed signal, said controlling means including:
  (i) operator control means for adjusting the values of a first subset of the parameters of said pulsed signal, said first subset of the parameters including signal current amplitude;
  (ii) first programming control means for establishing the values of a second subset of the parameters of said pulsed signal including signal modulation amplitude, on time, off time, rise time, signal modulation rate, type of signal modulation, signal pulse width, and signal pulse frequency;
  (iii) second programming control means for selectively initiating and terminating access to said first programming control means, wherein upon termination of access to said first programming control means, the values of said second subset of the parameters may not be varied until access to said first programming control means is initiated; and
(c) a microprocessor, operatively connected to said first and second programming control means, wherein said first and second programming control means supplies input data to said microprocessor, said microprocessor operatively connected to a non-volatile electrically erasable programmable read only memory to store parameters.

2. An electrical stimulator for use by a human patient, comprising:
(a) first means for generating a pulsed signal, said pulsed signal having parameters including an amplitude, a pulse width and a frequency; and
(b) second means cooperatively connected to said first means for controlling the parameters of said pulsed signal, said second means including:
  (i) operator control means for adjusting the values of a first set of the parameters of said pulsed signal generated by said first means, said first set of pulsed signal parameters includes signal current amplitude, and
  (ii) programming control means for establishing the values of a second set of the parameters of said pulsed signal, whereby the values of the parameters of the pulsed signal generated by said first means is determined by the values of the first and second set of parameters, said second set of said pulsed signal parameters includes signal modulation amplitude, on time, off time, rise time, signal modulation rate, type of signal modulation, signal pulse width, and signal pulse frequency and wherein said second means for controlling said pulsed signal parameters is a microprocessor, said microprocessor having a non-volatile electrically erasable programmable read only memory to store parameter sets, and wherein the adjustment of said pulsed signal parameters within said second set is accomplished by means of a plurality of potentiometers, each potentiometer corresponding to a specific pulsed signal parameter, said potentiometers thereby serving as said programming control means.

3. The electrical stimulator of claim 2 wherein the parameter values within said second set of pulsed signal parameters may vary over a range to permit use of the electrical stimulator as either a transcutaneous electrical nerve stimulator or as a muscle stimulator.

4. The electrical stimulator of claim 3 wherein the parameter values within said first set of pulsed signal parameters are limited by maximum values, whereby the stimulator will be safe to the patient utilizing the stimulator regardless of the adjustment to said operator control means.

5. The electrical stimulator of claim 4 wherein said pulsed signal parameter values within said first set of pulsed signal parameters may be selectively adjusted by the patient by said operator control means, said first set of pulsed signal parameters determining elementary parameters and second set of parameters determining less elementary parameters.

6. An electrical stimulator for use by a human patient, comprising:
(a) means for generating a pulsed signal, said pulsed signal having parameters including an amplitude, a pulse width and a frequency, the parameters having values;
(b) means, cooperatively connected to said generating means, for controlling the parameters of said pulsed signal, said controlling means including:
  (i) operator control means for adjusting the values of a first subset of the parameters of said pulsed signal, said first subset of the parameters including signal current amplitude;
  (ii) first programming control means for establishing the values of a second subset of the parameters of said pulsed signal including signal modulation amplitude, on time, off time, rise time, signal modulation rate, type of signal modulation, signal pulse width, and signal pulse frequency.
wherein said first programming control means comprise a plurality of potentiometers, whereby the adjustment of said second subset of the parameters is accomplished by means of said potentiometers, each of said potentiometers corresponding to a specific parameter of said pulsed signal; and
  (iii) second programming control means for selectively initiating and terminating access to said first programming control means, wherein upon termination of access to said first programming control means, the values of said second subset of the parameters may not be varied until access to said first programming control means is initiated.

7. The electrical stimulator of claim 1, wherein said first programming control means comprise a plurality of potentiometers, whereby the adjustment of said second subset of the parameters is accomplished by means of said potentiometers, each of said potentiometers corresponding to a specific parameter of said pulsed signal, and wherein said potentiometers establish signals which are acted on by said microprocessor, wherein the values of said second subset of the parameters are variable over a range to permit use of the electrical stimulator as either a transcutaneous electrical nerve stimulator or as a muscle stimulator.

8. The electrical stimulator of claim 7, wherein the values of said second subset of the parameters are limited by maximum values, whereby said pulsed signal will be safe to the patient utilizing the stimulator regardless of adjustment to said operator control means.

9. The electrical stimulator of claim 1, wherein said first programming control means comprise a plurality of contact switches, whereby the adjustment of said second subset of the parameters is accomplished by means of said switches, each of said switches corresponding to a specific parameter of said pulsed signal.

10. The electrical stimulator of claim 9, wherein said switches establish signals which are acted on by said microprocessor, whereby the values of said second subset of the parameters are variable over a range to permit use of the electrical stimulator as either a transcutaneous electrical nerve stimulator or as a muscle stimulator.

11. The electrical stimulator of claim 10, wherein the values of said second subset of the parameters are limited by maximum values, whereby said pulsed signal will be safe to the patient utilizing the stimulator regardless of adjustment to said operator control means.

12. An electrical stimulator for use by a human patient, comprising:
  (a) means for generating a pulsed signal, said pulsed signal having parameters including an amplitude, a pulse width and a frequency, the parameters having values;
  (b) means, cooperatively connected to said generating means, for controlling the parameters of said pulsed signal, said controlling means including:
    (i) operator control means for adjusting the values of a first subset of the parameters of said pulsed signal, said first subset of the parameters including signal current amplitude;
    (ii) first programming control means for establishing the values of a second subset of the parameters of said pulsed signal including signal modulation amplitude, on time, off time, rise time, signal modulation rate, type of signal modulation, signal pulse width, and signal pulse frequency;
    (iii) second programming control means for selectively initiating and terminating access to said first programming control means, wherein upon termination of access to said first programming control means, the values of said second subset of the parameters are stored in a non-volatile memory, whereby inadvertent patient modification of the values of said second subset of parameters is prevented; and
  (c) a microprocessor, operatively connected to said first and second programming control means and said operator control means, wherein said first and second programming control means and said operator control means supplies input data to said microprocessor, said microprocessor including an internal non-volatile electrically erasable programmable read only memory to store said second subset of parameters.

* * * * *

UNITED STATES PATENT AND TRADEMARK OFFICE
CERTIFICATE OF CORRECTION

PATENT NO. : 4,926,865

DATED : May 22, 1990

INVENTOR(S) : PAUL S. OMAN

It is certified that error appears in the above-identified patent and that said Letters Patent is hereby corrected as shown below:

Title Page:
In Item [57], Abstract, line 2, for "mircocomputer-based" read
    --microcomputer-based--.
Column 4, line 50, for "TUE" read --THE--.
Column 6, line 13, for "/circuit" read --circuit--.
Column 6, line 15, delete "data".
Column 6, line 18, after "transmitted" insert --along signal path 16,--.
Column 6, delete lines 21-25.
Column 6, line 26, delete "(pins 57 and 56, respectively) on chip 2".
Column 7, line 49, for "pus-button" read --push-button--.
Column 9, line 21, after "of" insert --latch-up--.
Column 10, line 17, for "t" read --timer which--.
Column 11, line 15, after "used" insert --for--.
Column 13, line 3, after "timing" delete ",".
Column 16, line 35, for "." read --,--.

Signed and Sealed this

Twenty-eighth Day of May, 1991

Attest:

HARRY F. MANBECK, JR.

*Attesting Officer*

Commissioner of Patents and Trademarks